(12) United States Patent
Borregaard

(10) Patent No.: US 8,491,761 B2
(45) Date of Patent: Jul. 23, 2013

(54) USE OF A SACRIFICIAL ANODE FOR CORROSION PROTECTION OF A PORTABLE DEVICE, E.G. A HEARING AID

(75) Inventor: Sune Pelle Borregaard, Smørum (DK)

(73) Assignee: Oticon A/S, Smorum (DK)

( * ) Notice: Subject to any disclaimer, the term of this patent is extended or adjusted under 35 U.S.C. 154(b) by 165 days.

(21) Appl. No.: 13/010,188

(22) Filed: Jan. 20, 2011

(65) Prior Publication Data

US 2011/0180421 A1 Jul. 28, 2011

Related U.S. Application Data

(60) Provisional application No. 61/297,296, filed on Jan. 22, 2010.

(30) Foreign Application Priority Data

Jan. 22, 2010 (EP) .................................. 10151393

(51) Int. Cl.
*C23F 13/14* (2006.01)
*H05K 3/32* (2006.01)

(52) U.S. Cl.
USPC .............. 204/196.37; 204/196.17; 204/196.3; 205/740; 29/846; 29/825; 29/832; 29/840

(58) Field of Classification Search
USPC .................. 204/271, 196.01, 196.02, 196.07, 204/196.1, 196.17, 196.23, 196.24, 196.25, 204/196.3, 196.37; 205/724, 725, 730, 732, 205/733, 740; 29/825, 832, 840, 846
See application file for complete search history.

(56) References Cited

U.S. PATENT DOCUMENTS

| | | | |
|---|---|---|---|
| 2,641,622 A | | 6/1953 | Higgins et al. |
| 5,260,146 A | * | 11/1993 | Savovic et al. .................. 429/65 |
| 6,019,877 A | | 2/2000 | Dupelle et al. |
| 7,097,746 B1 | * | 8/2006 | Tzviskos et al. ........ 204/196.23 |
| 7,599,192 B2 | * | 10/2009 | Pennaz et al. ................. 361/761 |
| 7,624,499 B2 | * | 12/2009 | Stole ............................... 29/832 |
| 2008/0122081 A1 | * | 5/2008 | Kim et al. ..................... 257/737 |

FOREIGN PATENT DOCUMENTS

| | | |
|---|---|---|
| DE | 197 14 847 A1 | 10/1998 |
| EP | 0 965 358 A2 | 12/1999 |

OTHER PUBLICATIONS

European Search Report issued in EP 10 15 1393 on Jun. 10, 2010.

* cited by examiner

*Primary Examiner* — Bruce Bell
(74) *Attorney, Agent, or Firm* — Buchanan Ingersoll & Rooney

(57) ABSTRACT

A portable device includes a substrate, a number of electronic components, and a battery having an anode and a cathode for energizing at least some of the components. The application further relates to a method of protection a portable device against corrosion and to the use of a portable device. An object of the present application is to protect selected metallic parts of a bodyworn electronic device against corrosion in a flexible and controlled manner. The problem is solved in that the portable device includes a sacrificial anode in the form of a component adapted to be surface mounted on the substrate. This has the advantage that corrosion can be contained at a specific location. The device may e.g. be used for portable listening devices, e.g. hearing aids or headsets or earphones including a part adapted for being worn at or in an ear of a user.

21 Claims, 4 Drawing Sheets

USE OF A SACRIFICIAL ANODE FOR CORROSION PROTECTION OF A PORTABLE DEVICE, E.G. A HEARING AID

CROSS-REFERENCE TO RELATED APPLICATIONS

The present application claims the benefit of U.S. provisional application Ser. No. 61/297,296, filed on Jan. 22, 2010, and claims the priority of EP application number 10151393.5, filed on Jan. 22, 2010. The entire contents of U.S. provisional application Ser. No. 61/297,296 and EP application number 10151393.5, are incorporated herein by reference.

TECHNICAL FIELD

The present application relates to portable electronic devices adapted to be worn at or on the body of a person, especially to the protection of metallic parts of such devices against corrosion. The application also relates to the use of a sacrificial anode for corrosion protection in a portable device. The application furthermore relates to a method of protecting a portable device against corrosion.

The disclosure may e.g. be useful in applications such as portable listening devices, e.g. hearing aids or headsets or earphones comprising a part adapted for being worn at or in an ear of a user.

BACKGROUND ART

In general, when an electrolytic solution comprising free, movable positively and negatively charged ions allowing the solution to conduct electric current (e.g. salt water) is brought into contact with two different metallic substances electrically connected to each other, the less noble metallic substance will corrode more than the more noble metallic substance (the 'degree of nobility' being e.g. defined by the activity or Galvanic series listing metals in descending order of the potential they develop in a given electrolyte against a standard reference electrode). The degree of 'nobility' of a metal as given by the activity series is based on how strongly its atoms are bound to the surface of the material (the stronger the bond, the more noble the material). A relatively less noble metallic substance X will relatively more easily (than the more noble metallic substance Y) give up atoms to the electrolytic solution in the form of positively charged ions ($X^{+n}$) and thereby relatively more easily corrode. The rate of corrosion depends on a range of parameters, including the potential difference in the activity series between the two metallic substances in question, the kind of and concentration of ions in the electrolytic solution, the area of the exposed parts, the temperature, etc. The less noble metal is said to constitute the anode and the more noble metal the cathode in an electrochemical corrosion process. This process is termed galvanic corrosion.

In case of the presence of two (e.g. identical) metallic substances in an electrolytic solution with a voltage difference applied between the two metallic substances (e.g. electric terminals or conductors on a substrate driven by different polarities of a battery or just having different potentials), the metallic substance having the more positive potential (the anode) will corrode the faster.

A hearing aid or other communication or listening device having a part located at or in the ear of a person is subject to a harsh environment with heat, moisture, sweat, etc. (the latter constituting an electrolytic solution comprising $Na^+$ and $Cl^-$ ions). Typically, the enclosure of the electronic components and the battery is not absolutely tight (although attempts are made to contrary). This leads to corrosion inside the hearing aid, if e.g. sweat is allowed to enter the device. The corrosion will occur at the locations where the electrolytic solution enter, e.g. 'guided' by capillary effects, e.g. by micro volumes or channels. Such micro volumes or channels can e.g. be present between a battery compartment or an external activation element (e.g. a push button) and an enclosure hosting a printed circuit board. The presence of an electrolytic solution combined with the relatively high energy (voltage difference in the order of one or more Volts) in the battery, makes it almost certain that—at some stage of the lifetime of the device—there will be a part of the device which is damaged by corrosion. If one area is protected better against corrosion than another area (e.g. by coating with a conventional coating process) the less protected area will be subject to corrosion instead. In other words, the corrosion problem "jumps" from one place to another, when the protection of a critical part is improved (relative to other parts). For example, if a corrosion problem on the battery contacts is fixed, then the battery casing itself may start to corrode.

The use of a 'sacrificial anode' is known from marine applications (e.g. outboard engines, underwater steel structures, ballast tanks on commercial ships, etc., cf. e.g. [Bardal; 1964], chapter 10.4, pp. 285-300) to prevent corrosion to attack e.g. steel parts exposed to salt water. A sacrificial anode is a metallic anode intended to be dissolved to protect other metallic components. The more (chemically) active metal (i.e. the metal having the least noble position in the activity series) is more easily oxidized than the protected metal and thus corrodes first (hence the term 'sacrificial').

U.S. Pat. No. 7,097,746 B1 describes an anode protection device in the form of a sacrificial anode plate located on a casing between positive and negative contact terminals of a device, e.g. a battery. In an embodiment, the sacrificial anodic plate is welded to the aluminium case of a rechargeable battery of a behind-the-ear (BTE) hearing device.

DISCLOSURE

It is proposed to provide a portable device, which is exposed to a humid and/or salty environment, with a "dumb" element that the corrosion can eat its way into without damaging any electronics or other features, which are important for the functioning and/or the aesthetic presentation of the device.

That "dumb" element is according to the invention a sacrificial anode, e.g. an SMD mountable anode, e.g. a Zink anode. The anode is e.g. placed on a substrate (e.g. a PCB) of the device.

Advantages comprise one of more of the following:
It can be applied automatically to the device (e.g. SMD mounted on a PCB).
You know exactly where the corrosion will appear (the corrosion can be contained).
Corrosion problems on existing "bad designs" can be prevented by adding this component.

An object of the present application is to protect selected metallic parts of a bodyworn electronic device against corrosion in a flexible and controlled manner.

Objects of the application are achieved by the invention described in the accompanying claims and as described in the following.

A Portable Device:
An object of the application is achieved by a portable device comprising a substrate, a number of electronic components, and a battery comprising an anode (plus terminal)

and a cathode (minus terminal) for energizing at least some of the components. The portable device further comprises a sacrificial anode.

This has the advantage that corrosion can be contained at a specific location.

The term 'a portable device' is in the present context taken to mean a device that is adapted to be portable by a human being, e.g. in that it weighs less than 5 kg, e.g. less than 1 kg, e.g. less than 500 g, e.g. less than 200 g, e.g. less than 10 g. A portable device is in the present context an electronic device in the sense that it comprises electronic components powered by an energy source (e.g. a battery) in the device. A portable device can e.g. be or comprise a part that is adapted for being worn in close contact with the human body (e.g. having contact with human skin), e.g. in or at an ear. A portable device can e.g. be a telephone or other listening device, e.g. a hearing instrument or an ear phone or a headset or an active ear protection device or an audio gateway or a combination thereof. A portable device can e.g. be a device that is in wireless communication with a remote device that is NOT worn by the same person that wears the portable device in question. A hearing instrument can e.g. comprise or be constituted by a behind the ear (BTE) part adapted to be located behind an ear or a user and/or an in the ear (ITE) part adapted to be located fully or partially at or in an ear canal of a user. In an embodiment, the hearing instrument comprises or is constituted by an ITE device adapted for being located fully or partially in the bony part of the ear canal.

In an embodiment, the sacrificial anode is located on or mounted on the substrate.

In an embodiment, the sacrificial anode is deposited on the substrate, e.g. in a process similar to the process whereby electrical conductors for connecting electronic components to be mounted on the substrate are deposited or printed on the substrate. In an embodiment, the same metallic substance is used for the metallic conductors as for the sacrificial anode, whereby the deposition can be made using the same process steps. In a particular embodiment, the sacrificial anode comprises one or more of Al or Cu or Zn. In a particular embodiment, the sacrificial anode is mainly constituted by Al or Cu or Zn.

The substrate can in principle be of any kind appropriate for hosting electronic components and their electric interconnections (i.e. typically comprising an upper layer of a dielectric material whereon the components and the pattern of electrical conductors connecting the components and power supply), e.g. a ceramic substrate. In an embodiment, the substrate is a printed circuit board (PCB), e.g. a flexible PCB ('flexprint').

In an embodiment, the material of the conductor(s) electrically connecting the sacrificial anode and the item to be protected by the sacrificial anode is the same as the material of either of the sacrificial anode and the item to be protected. In an embodiment, the material of the conductor(s) electrically connecting the sacrificial anode and the item to be protected by the sacrificial anode is a material which is more noble than the material constituting the sacrificial anode. In an embodiment, the material of the conductor(s) electrically connecting the sacrificial anode and the item to be protected by the sacrificial anode is a material which is less noble than the material constituting the item to be protected.

In a particular embodiment, the sacrificial anode is implemented as a component adapted for being surface mounted on the substrate. In a particular embodiment, the sacrificial anode is implemented as an SMD-component comprising one or more terminals adapted for being soldered or welded to corresponding conductors (e.g. one or more pads) on a substrate (e.g. a PCB). In an embodiment, the sacrificial anode comprises one or more elements selected from the group comprising Cu, Al, and Zn (or Fe, Mg, Ni or Sn). In an embodiment, the sacrificial anode comprises a rectangular plate of a predefined area and thickness. In an embodiment, the SMD-component comprises a housing for enclosing (at least an upper part, NOT intended for facing the substrate) the sacrificial anode, the housing e.g. comprising an insulating material (e.g. a ceramic or plastic material), and e.g. an electric screen. The SMD component (and or the substrate) comprising the sacrificial anode is preferably adapted to provide that an electrolytic solution present on the substrate can come into contact with the sacrificial anode when the component is mounted on the substrate. Preferably, a certain minimum distance between a sacrificial anode (component) and components or conductors on the substrate NOT intended to be influenced by the sacrificial anode is arranged. In an embodiment, the sacrificial anode of the SMD component is adapted to be in physical contact with the substrate, when mounted on said substrate. In an embodiment, the sacrificial anode of the SMD component is adapted to be physically separated from the substrate a distance that is adapted to utilize capillary effects to attract possible electrolytic solution to the volume between the sacrificial anode of the SMD component and the substrate, whereby the component serves the dual purpose of removing electrolytic solution from other parts of the substrate and containing it there by the chemical reaction with the sacrificial anode. The distance of separation between substrate and sacrificial anode should be adapted to the materials of the substrate, sacrificial anode and the expected electrolytic solution. Said distance of separation is taken to mean the distance intended to be present when an (new) SMD component comprising a sacrificial anode is (initially) mounted on the substrate.

In a particular embodiment, the SMD component further comprises a reservoir for containing excess electrolytic solution. This may be particularly advantageous in an embodiment, where the sacrificial anode comprises one or more specifically adapted holes to allow such excess electrolytic solution to be soaked up from the volume between the substrate and the sacrificial anode of the component via capillary effects. In an embodiment, at least a part of the sacrificial anode comprises a multitude, e.g., an array, of such holes. In an embodiment, the SMD component is adapted to allow air to escape from the reservoir, e.g. in that it comprises one or more openings for this purpose.

In a particular embodiment, the sacrificial anode is adapted for protecting an electric contact terminal connected to the battery. In a particular embodiment, the sacrificial anode is electrically connected to the anode of the battery. In a particular embodiment, the sacrificial anode is located on the substrate in the vicinity of the positive and negative terminals of the battery, e.g. having substantially equal minimum distances between peripheries of the sacrificial anode and the respective contact terminals (connecting pads) to the battery. In a particular embodiment, the sacrificial anode is located on the substrate between the positive and negative terminals of the battery.

In an embodiment, the sacrificial anode is a formed as a piece or component that is separate from the battery. In an embodiment, the battery comprises an sacrificial anode in addition to the (normal) anode of the battery, such possible sacrificial anode being in addition to the sacrificial anode of the present disclosure.

In a particular embodiment, the sacrificial anode comprises a metal that is less noble—with a view to the activity series—than the metal constituting the major part of the item to be protected against corrosion by the sacrificial anode. In a particular embodiment, the sacrificial anode comprises a metal that is less noble than the metal constituting the major part of the electrical contact connected to the anode and/or cathode of the battery.

In an embodiment, the battery is a rechargeable battery (e.g. a NiMH battery or a Li-Ion battery). In this case the same battery is expected to be located for a longer time (possibly throughout the lifetime of the device) in the device than if an ordinary (non-rechargeable) battery is used. Hence the need for protection against corrosion is larger (other things being equal). In an embodiment, the battery is an ordinary (non-rechargeable) battery, e.g. a zinc-air battery or an alkaline or a silver oxide battery.

Preferably, the sacrificial anode is designed to have a size and form sufficient for providing active protection against corrosion of the terminal(s) connected to the sacrificial anode in the operational life-time of the device or part of a device in question. In an embodiment, the sacrificial anode is designed to have a size and form sufficient for providing active protection against corrosion of the terminal(s) connected to the sacrificial anode in the expected mean time between service checks of the device in question.

Use:

Use of a sacrificial anode for corrosion protection in a portable device is furthermore provided by the present application. In an embodiment, the sacrificial anode is implemented as a surface mount component (SMD). In particular use in a portable device for protecting an electrical contact terminal to a battery is provided.

In a particular embodiment, use of a portable device described above, in the detailed description of 'mode(s) for carrying out the invention' and in the claims is provided.

In a particular embodiment, use in a listening device comprising a part adapted for being worn at or in the ear of a user is provided.

A Method:

A method of protecting a portable device against corrosion is moreover provided by the present application. The method comprises providing a substrate; providing a number of electronic components; providing a battery comprising an anode (plus terminal) and a cathode (minus terminal) for energizing at least some of the components; and providing a sacrificial anode.

It is intended that the structural features of the device described above, in the detailed description of 'mode(s) for carrying out the invention' and in the claims can be combined with the method, when appropriately substituted by a corresponding process and vice versa. Embodiments of the method have the same advantages as the corresponding devices.

In an embodiment, the method further comprises providing that the sacrificial anode comprises a metal that is less noble—with a view to the activity series (and to the expected electrolytic solution)—than the metal constituting the major part of the item to be protected against corrosion by the sacrificial anode; and electrically connecting the sacrificial anode to the item to be protected against corrosion.

In a particular embodiment, the method comprises providing that the sacrificial anode is formed or mounted on the substrate.

In a particular embodiment, the method comprises electrically connecting the sacrificial anode to the anode of the battery.

In a particular embodiment, the method comprises providing that the sacrificial anode is formed as a surface mount device, SMD.

In a particular embodiment, the method comprises providing that a distance between the sacrificial anode and the substrate—when the (SMD-) component is initially mounted on the substrate—is adapted to provide that electrolytic solution is soaked up via capillary effects.

In a particular embodiment, the SMD component further comprises a reservoir for containing excess electrolytic solution. This may be particularly advantageous in an embodiment, where excess electrolytic solution is soaked up from the volume between the substrate and the sacrificial anode of the component via capillary effects, and the sacrificial anode comprises one or more specifically adapted holes to allow such excess electrolytic solution to be soaked up from the volume between the substrate and the sacrificial anode of the component via capillary effects. In an embodiment, at least a part of the sacrificial anode comprises a multitude, e.g., an array, of such holes. In an embodiment, the SMD component is adapted to allow air to escape from the reservoir, e.g. in that it comprises one or more openings for this purpose.

Further objects of the application are achieved by the embodiments defined in the dependent claims and in the detailed description of the invention.

As used herein, the singular forms "a," "an," and "the" are intended to include the plural forms as well (i.e. to have the meaning "at least one"), unless expressly stated otherwise. It will be further understood that the terms "includes," "comprises," "including," and/or "comprising," when used in this specification, specify the presence of stated features, integers, steps, operations, elements, and/or components, but do not preclude the presence or addition of one or more other features, integers, steps, operations, elements, components, and/or groups thereof. It will be understood that when an element is referred to as being "connected" or "coupled" to another element, it can be directly connected or coupled to the other element or intervening elements maybe present, unless expressly stated otherwise. Furthermore, "connected" or "coupled" as used herein may include wirelessly connected or coupled. As used herein, the term "and/or" includes any and all combinations of one or more of the associated listed items. The steps of any method disclosed herein do not have to be performed in the exact order disclosed, unless expressly stated otherwise.

BRIEF DESCRIPTION OF DRAWINGS

The disclosure will be explained more fully below in connection with a preferred embodiment and with reference to the drawings in which.

The figures are schematic and simplified for clarity, and they just show details which are essential to the understanding of the disclosure, while other details are left out. Throughout, the same reference names are used for identical or corresponding parts.

Figure 1A:
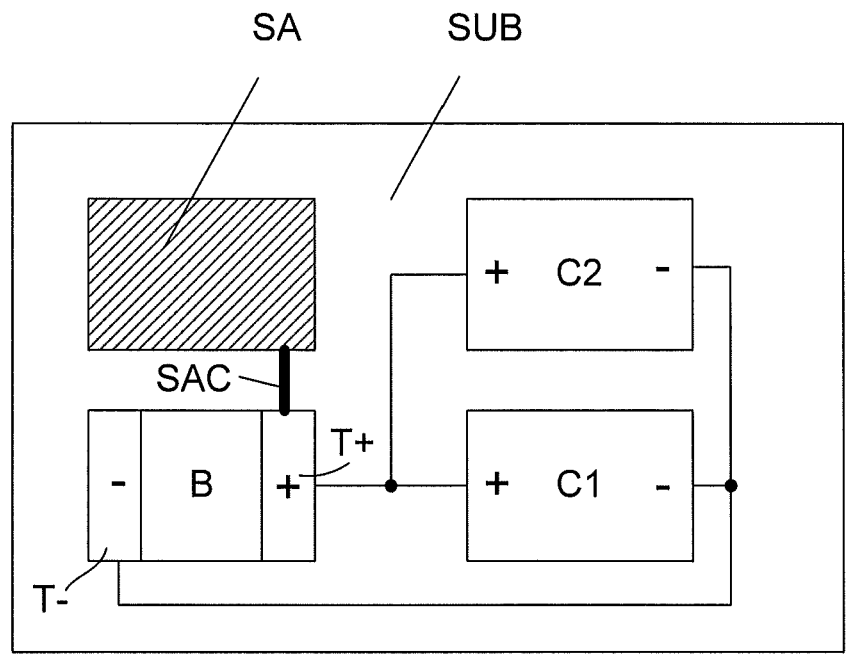
FIGS. 1a and 1b show embodiments of a portable device comprising a substrate and a battery and a sacrificial anode as suggested in the present application.

Further scope of applicability of the present disclosure will become apparent from the detailed description given hereinafter. However, it should be understood that the detailed description and specific examples, while indicating preferred embodiments of the disclosure, are given by way of illustration only, since various changes and modifications within the spirit and scope of the disclosure will become apparent to those skilled in the art from this detailed description.

MODE(S) FOR CARRYING OUT THE INVENTION

The purpose of the sacrificial anode is to provide (galvanic) corrosion protection of electronics, e.g. the parts having (essentially) the same electric potential (battery voltage) as the sacrificial anode, e.g. the contacts and conductors connected to the (more) positive voltage of the battery.

Preferably, the sacrificial anode is designed to have a size and form sufficient for providing active protection against corrosion of the terminal(s) connected to the sacrificial anode in the life-time of the device or part of a device in question. Such design is preferably performed with a view to the potential difference in the activity series between the two metallic substances constituting the sacrificial anode and the item to be protected, the expected kind of and concentration of ions in the electrolytic solution, the area of the exposed parts, the temperature, the battery voltage, the power consumption, etc. (cf. e.g. chapter 10.4.3-10.4.5 on pages 292-300 of [Bardal; 1994]).

Many electronic devices incorporate printed circuit boards (PCB) whereon electronic components are mounted directly onto one or both sides using a Surface Mount Technology (SMT) (as opposed to mounting technologies e.g. involving pins extending through holes in the PCB). Components that are specifically adapted for being surface mounted are typically physically smaller than corresponding components with pins. The use of surface mount components is in general an advantage where relatively small dimensions and a relatively high degree of automation in the mounting process is an advantage. Electronic components adapted for being surface mount are sometimes referred to as SMC (Surface Mount Components) but also as SMD (Surface Mount Device) components. The latter term is used in the present application. An SMD component has electrical terminals in the form of metallised areas (e.g. in the form of end caps) suitable for being soldered (typically by a machine) directly onto solderable electrically conducting pads ('footprints') on the surface of a substrate provided with solder paste for receiving a particular SMD component (the substrate, e.g. a PCB, typically having predefined electrically conducting patterns for interconnecting the various SMD components on the substrate and possibly for connecting the circuitry to external parts).

In an embodiment, the sacrificial anode is an SMD (pick and place) mountable sacrificial anode. In an embodiment, the sacrificial anode is connected to one of the battery terminals, e.g. to the anode. In an embodiment, the terminals of the battery comprise iron or steel (e.g. in that a major part, such as above 90%, is iron or steel).

Figure 1B:
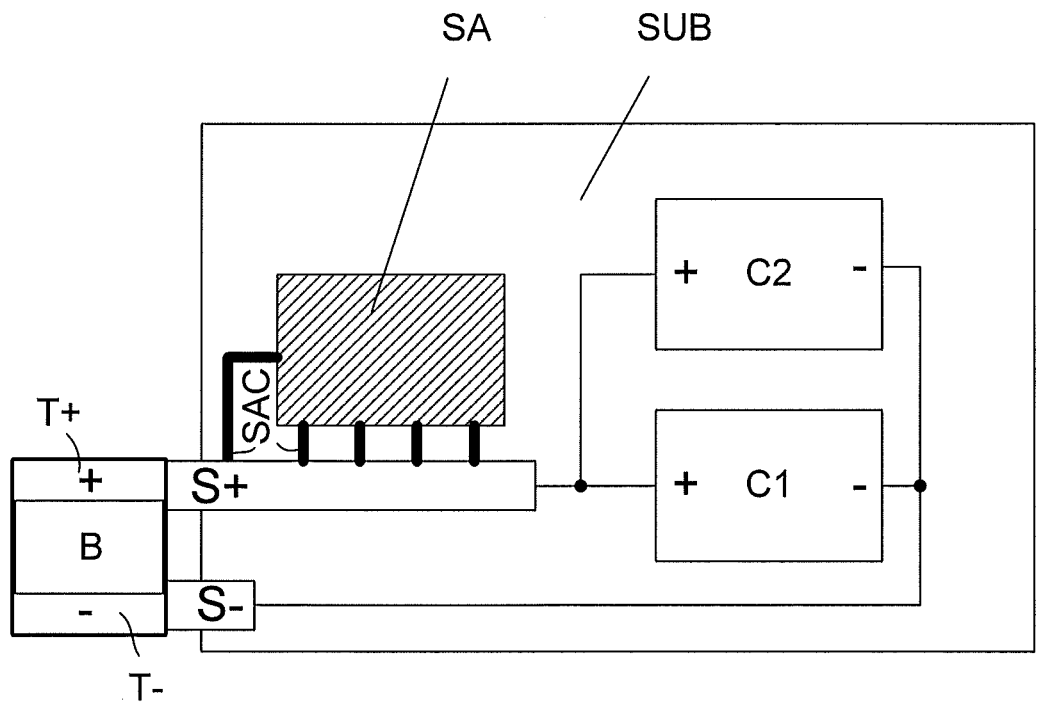

FIG. 1 shows different embodiments of a portable device comprising a substrate and a battery and a sacrificial anode as suggested in the present application. FIG. 1 shows a substrate SUB comprising two electronic components C1, C2, a battery B and a sacrificial anode SA. The battery comprises a positive and a negative terminal T+, T−, respectively (the terminal denoted '+' referring to the anode having a larger (more positive) electrostatic potential than the cathode denoted '−'). The battery is electrically connected (e.g. soldered or by establishing a contact pressure) to conductors on the substrate via terminals T+ and T− on the battery. The battery voltage is distributed to corresponding terminals '+' and '−' on the electronic components C1, C2. The positive terminal T+ on the substrate is electrically connected to the sacrificial anode SA via electrical connection SAC to protect it against corrosion. In an embodiment, the positive terminal T+ is made essentially of a low grade stainless steel (e.g. an alloy comprising Fe and Ni). In an embodiment, the corresponding sacrificial anode SA is made essentially of Zn. Thereby the sacrificial anode is less noble than the positive terminal (and the battery casing, which is e.g. made of a low grade steel) AND the electrical conductors on the substrate, which are typically based on Cu, but alternatively can be made of or comprise other elements, e.g. one or more of Al or Au or Ag. Thereby corrosion can be expected to be mainly confined to the sacrificial anode. In a particular embodiment, the sacrificial anode is made as an SMD component whereby it can be (e.g. machine) mounted in the same process as the components C1, C2, which represent electronic components or (possibly mixed analogue digital) integrated circuits. In an embodiment, the electrical connection SAC between the protected item and the sacrificial anode is made of a material that is less noble than the conductors (e.g. mainly Cu) on the substrate (e.g. a PCB) connecting the electronic components C1, C2. In an embodiment, the electrical conductor constituting the SAC is wider than the normal conductors on the substrate connecting the electronic components C1, C2 and/or is distributed on a number of conductors between the item to be protected and the sacrificial anode (cf. e.g. FIG. 1b comprising five parallel SAC conductors).

FIG. 1b shows an embodiment similar to that of FIG. 1a. The only difference is that the battery B is not mounted on the substrate (as in FIG. 1a), but is e.g. located in a battery compartment (e.g. a battery drawer) for easy replacement. The battery terminals T+, T− are electrically connected to corresponding terminals S+, S− on the substrate. Further the terminal S+ (which is typically made of a high grade stainless steel) is electrically connected to the sacrificial anode SA via electrical connections SAC to protect it against corrosion. The electrical connections SAC comprise one wide or several (here five) independent electrical conductors of relatively smaller width, depending on the practical layout of the substrate. By using a sacrificial anode, the material quality of the contacts S+, S− can optionally be lowered (to a certain extent) without inducing corrosion.

In the embodiments of FIG. 1a (and 1b), only the conductors related to power distribution and connection to the sacrificial anode are shown. Other conductors for electrically connecting the functional ports of the components are not shown. They may be present on the same substrate or on another layer of a layered substrate (e.g. on the opposite side of a single layer substrate).

FIG. 2 shows various embodiments of a sacrificial anode SA formed as an SMD component SMD-SA.

Figure 2A:
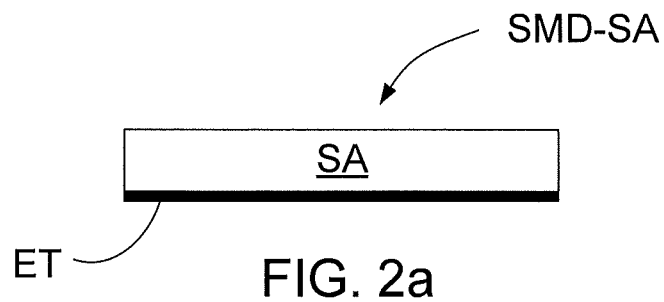
FIGS. 2a-2e show various embodiments of a sacrificial anode formed as a SMD component
Figure 2B:
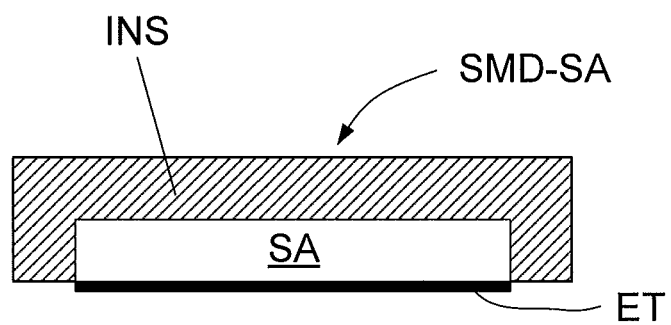
Figure 2C:
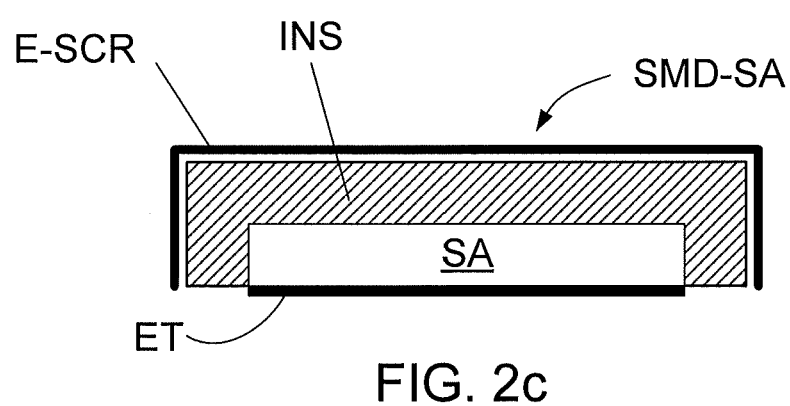
Figure 2D:
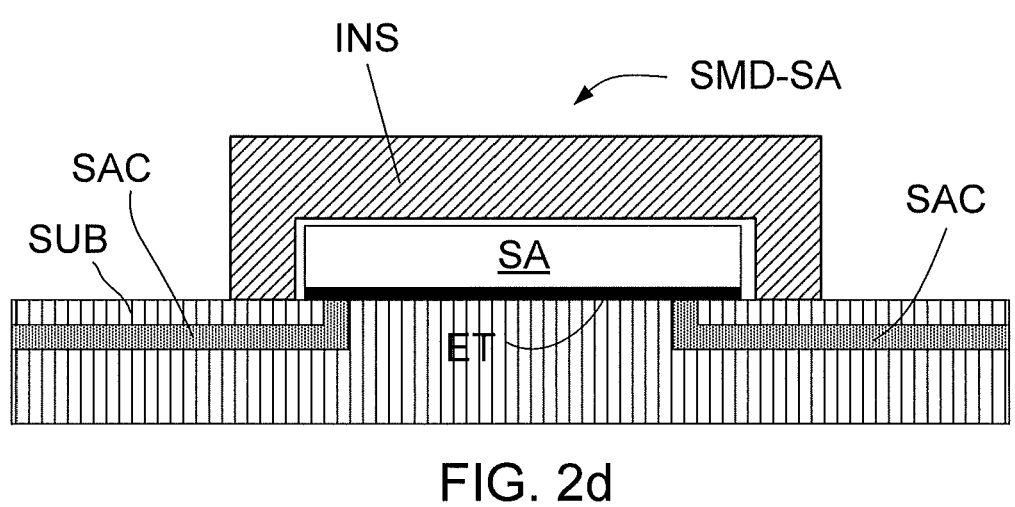
Figure 2E:
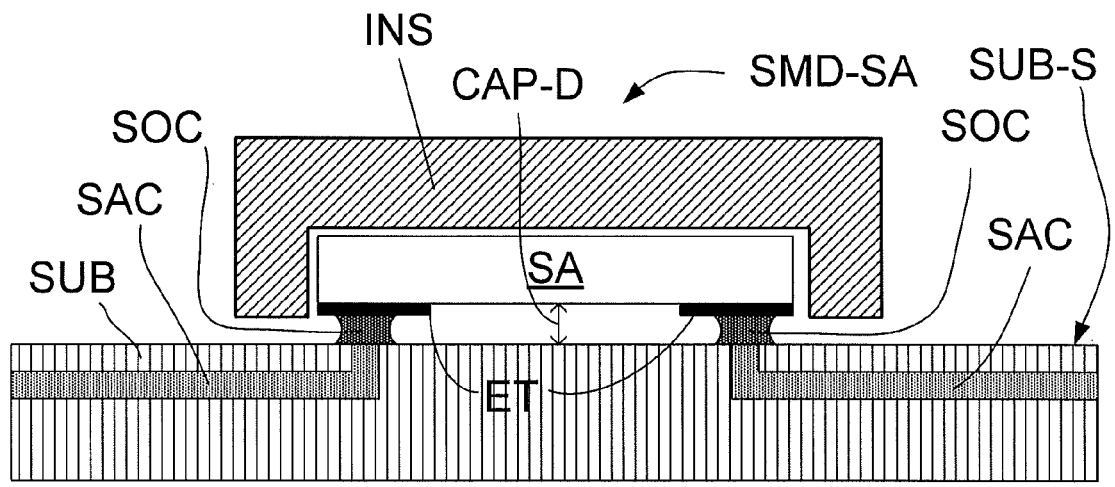

FIG. 2a shows an embodiment of a sacrificial anode formed as an SMD component SMD-SA in a simple form comprising a plate of a metal constituting a sacrificial anode SA and a layer of soldering or welding material ET applied to one of the faces of the metal plate and adapted for being soldered or welded to a substrate in a surface mounting process. In an embodiment as shown in FIG. 2b, the SMD component further comprises a housing INS comprising an electrically insulating material (and possibly an electromagnetic screen as shown in FIG. 2c). The embodiment of a sacrificial anode SA formed as an SMD component SMD-SA shown in FIG. 2c comprises an electromagnetic screen intended for avoiding the pick up by the SMD-SA of electromagnetic radiation from possible noisy components (e.g. radio parts) in the environment of the sacrificial anode. FIG. 2d shows an embodiment of an SMD-SA component mounted on a substrate SUB. The terminal ET of the sacrificial anode plate SA is soldered onto a corresponding pad or pads on the substrate. The electrical connections SAC to the item to be protected are here shown to run in an intermediate layer of the substrate (not on the surface of the substrate). They may alternatively run on a (upper or lower) surface of the substrate. The SMD-SA component comprises a housing INS, which at least on some of the sides of the SMD-SA component (depending on the practical layout) may be in physical contact with the substrate to form a barrier for minimizing the possible diffusion of electrolytic solution and/or anodic reaction products out to other parts of the substrate. On the other hand the component should allow the entrance of electrolytic solution to come in contact with the sacrificial anode SA (e.g. by avoiding such barrier on one of the sides of the SMD-SA component, e.g. a side facing the item to be protected). FIG. 2e shows an embodiment of an SMD-SA component mounted on a substrate SUB. The embodiment of FIG. 2e is identical to the one shown in FIG. 2d apart from the SMD-SA component of FIG. 2e being mounted on the substrate to provide a predefined distance CAP-D between the sacrificial anode SA and the substrate surface SUB-S. The predefined distance CAP-D is adapted to provide that an electrolytic solution (or at least a part thereof) arriving at the SMD-SA component is soaked into the volume between the sacrificial anode SA and the substrate surface SUB-S, and maintained there for chemical reaction with the sacrificial anode SA. An appropriate value of the distance CAP-D can e.g. be determined by experiment with a view to the surface materials of the components and substrate (including possible deposited structures, e.g. electric conductors) and the electrolytic substance expected to arrive at the substrate. In an embodiment, the distance is larger than 0.05 mm, such as larger than 0.1 mm, such as larger than 0.5 mm. In an embodiment, the distance CAP-D is smaller than 2 mm, such as smaller than 1 mm, such as smaller than 0.5 mm. In an embodiment, the distance CAP-D is in the range from 0.05 mm to 2 mm, such as in the range from 0.1 mm to 1 mm. The terminals ET of the sacrificial anode plate SA are soldered onto corresponding pads on the substrate providing solder connections SOC (or as shown in FIG. 2e soldered to via connections to another layer of the substrate) to connect to electrical connections SAC to the item to be protected against corrosion.

Instead of one electric terminal as shown in FIG. 2a-FIG. 2d, the SMD component SMD-SA may comprise a number of electric terminals ET (e.g. 2 or 4 or 8 or more), e.g. distributed around the periphery of the component (or along one or more sides of the component depending on the actual layout) and adapted for being connected to corresponding contact pads or areas on the substrate for establishing electrical contact to the item(s) on a substrate intended for being protected against corrosion. The terminal(s) ET of the SMD component SMD-SA is/are adapted for being soldered or welded to conductors or pads on a substrate by an automatic process (e.g. together with other components of the substrate, cf. C1, C2 of FIG. 1 or C1, C2 and IC of FIG. 3). Preferably the material(s) chosen for forming the connection(s) between the sacrificial anode and the item to be protected, i.e. the electrical conductors on the substrate and the soldering or welding material of the contact pads or areas, is/are chosen with a view to minimizing the risk of corrosion. The sacrificial anode can take on any form, but is typically formed as a plate (or mesh or web), e.g. a rectangular plate, of a predetermined initial thickness. The (initial) thickness of the plate (or web) SA is typically less than 5 mm. In an embodiment, the plate SA is (initially) at least 0.1 mm, such as at least 0.5 mm, such as at least 1 mm thick. In an embodiment, the thickness of the plate SA is (initially) in the range from 0.1 mm to 1 mm. The area of the plate (or web) SA is typically less than 100 $mm^2$, such as less than 50 $mm^2$, such as less than 25 $mm^2$. In an embodiment, the plate SA has a surface area of at least 2 mm by 2 mm. In an embodiment, the plate SA is made essentially of Zn. In an embodiment, the sacrificial anode is fully or partially formed as a web or mesh (or comprises a part that is formed as a web or mesh). This is particularly advantageous in combination the embodiment shown in FIG. 2e, where the sacrificial anode is mounted a distance CAP-D from the substrate surface SUB-S. This has the advantage of providing an improved adhesion of the electrolytic substance, which in combination with the capillary effect provides an improved containment of the corrosive action to the sacrificial anode of the SMD-component SMD-SA.

The SMD component SMD-SA is e.g. used for corrosion protection in a part of a hearing aid adapted for being located behind or at or in an ear of a user and therefore exposed to a salty and humid environment at relatively high temperatures in the 20 to 40 degree range).

Figure 3:
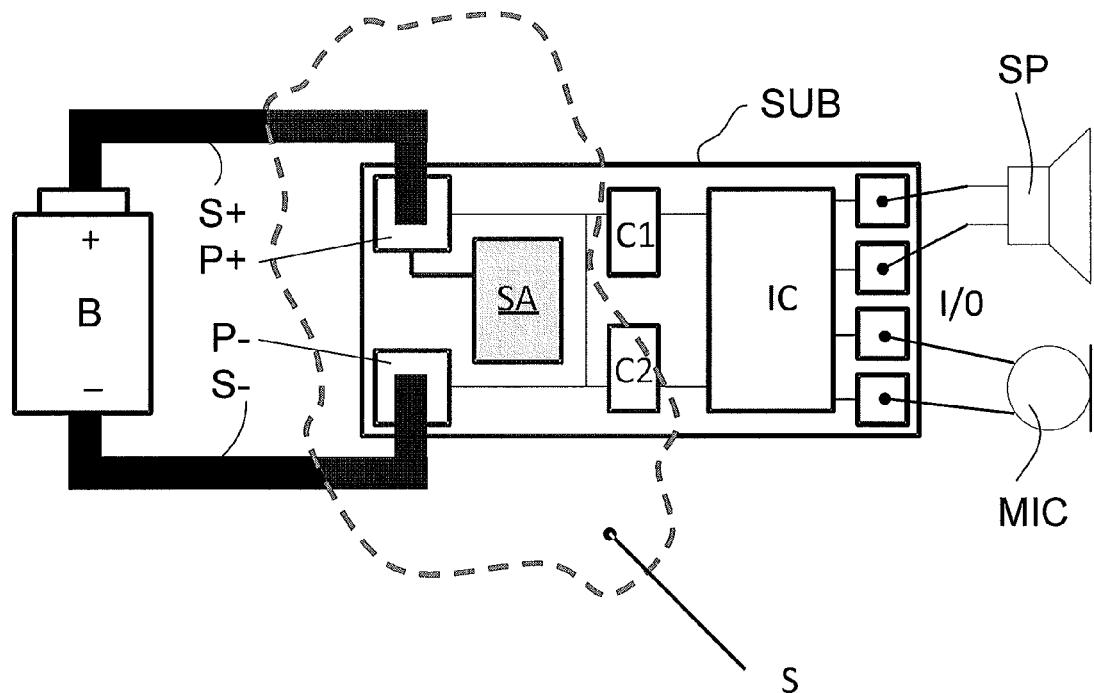
FIG. 3 shows an embodiment of a portable device comprising a substrate and a battery and a sacrificial anode.

FIG. 3 shows an embodiment of a portable device comprising a substrate SUB, a sacrificial anode SA and a number of electric or electronic components C1, C2 and IC mounted and electrically connected on the substrate, and a battery B which is separate from the substrate but electrically connected to pads P+, P− on the substrate via battery contact elements S+ and S− electrically connecting the pads P+, P− to the positive (+) and negative (−) battery voltage, respectively. The substrate further comprises a number of I/O pads (here 4 are shown, but more will typically be present) electrically connected to the electronic circuitry on the PCB (here to the component IC representing an integrated circuit, e.g. comprising processor, amplifier and driver circuitry). The I/O pads are e.g. connected to transducer components in the form of a microphone MIC and a speaker SP. Other components could be connected to the I/O pads instead of or in addition to the microphone and speaker components, e.g. a telecoil or other antenna elements for establishing a wireless interface to another device. The transducers are here shown NOT to be mounted on the substrate SUB, but one or both of them may be mounted on the substrate in other embodiments. A pool of electrolytic solution S (e.g. sweat from a human being) is shown to cover parts of the substrate SUB including the battery pads P+, P− and part of the terminals S+, S−, the sacrificial anode SA and part of the component C2 and part of the electrical conductors connecting the components of the substrate. Thereby the galvanic corrosion process is activated and the sacrificial anode SA will minimize the corrosion of the protected item(s), here in particular the positive contact terminal of the battery (which is the more exposed to corrosion, due to its higher electrostatic potential in the presence of the electrolytic solution S (salt water)). FIG. 3 may e.g. illustrate parts of a hearing aid, e.g. of an in the ear (ITE) or behind the ear (BTE) type hearing aid, but can relate to any other portable device comprising a battery and electronic circuitry. In an embodiment, the microphone MIC or the speaker SP (or both) is e.g. not present in this part of the device.

Figure 4:
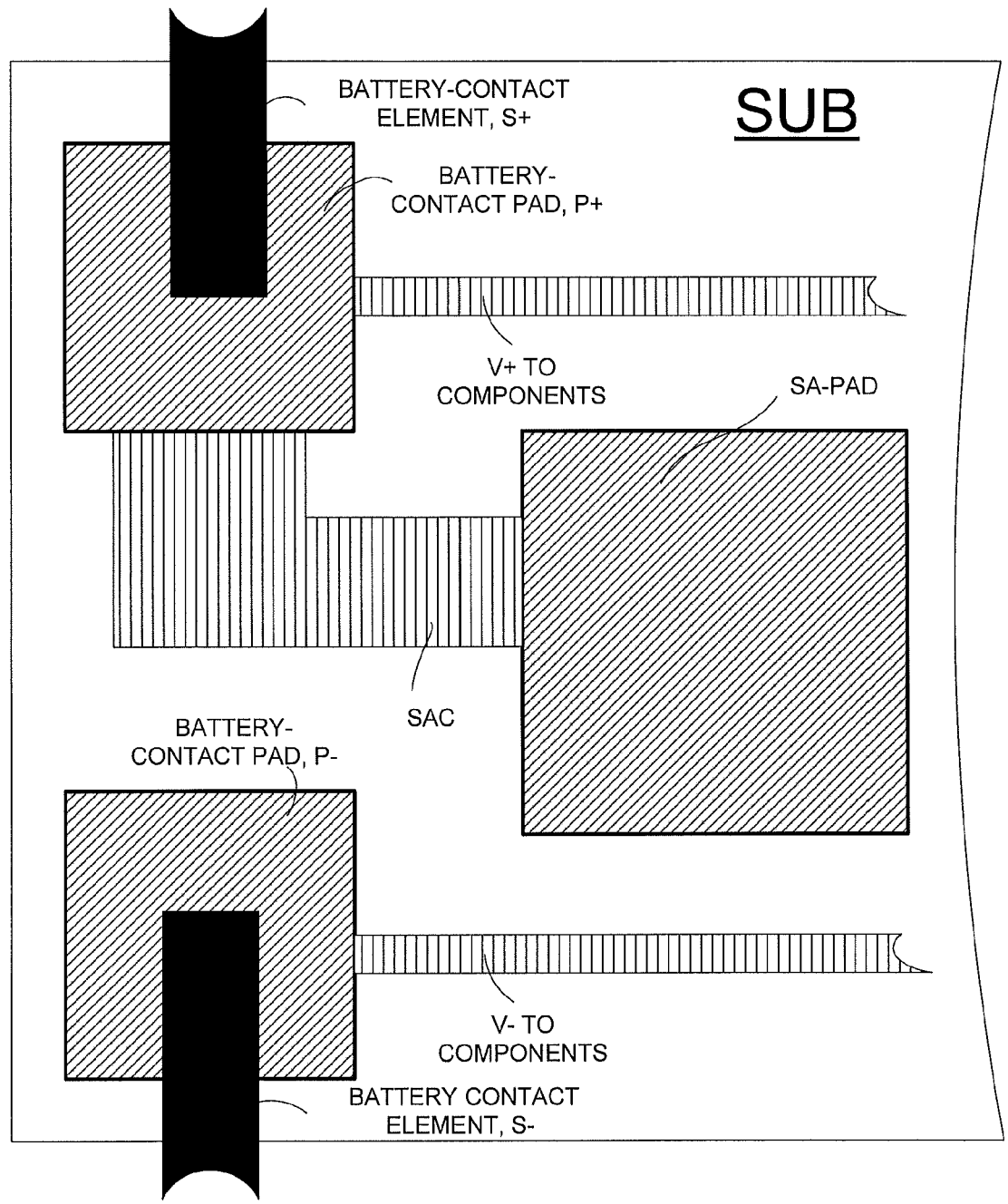
FIG. 4 shows a partial layout of a substrate of a portable device as shown in FIG. 3.

FIG. 4 shows a partial layout of a substrate of a portable device as shown in FIG. 3. The part of the substrate layout shown is a part corresponding to the leftmost part of the substrate SUB of FIG. 3 comprising the footprint of the electrical connections to the battery (8) and to the sacrificial anode component (SA) (e.g. an SMD-SA, e.g. as shown in FIG. 2). The layout comprises BATTERY CONTACT PADs P+ and P− for receiving BATTERY CONTACT ELEMENTs S+ and S− (e.g. resilient contact members of a high grade steel), respectively, for connecting the pads to the positive and negative voltage terminals (T+, T−) of the battery (B), respectively (cf. FIG. 1). The BATTERY CONTACT ELEMENTs S+ and S− comprise e.g. pre-coated or pre-plated terminals adapted for being e.g. soldered to the contact pads P+, P−. The layout further comprises a pad SA-PAD for connecting to the sacrificial anode component (via terminal ET, cf. e.g. FIG. 2)). The pads comprise e.g. Au. The solder material (cf. e.g. SOC in FIG. 2) comprises e.g. mainly Sn (e.g. more than 97%) and smaller amounts of Ag and/or Cu. The BATTERY CONTACT PAD P+ and the sacrificial anode pad SA-PAD are electrically connected via electrical conductor SAC (here running on a surface of the substrate). Electrical conductors from the BATTERY CONTACT PADs P+, P− to respective battery inputs on components of the substrate (cf. e.g. FIG. 1) are indicated as V+ TO COMPONENTS and V− TO COMPONENTS, respectively, and only shown in partial (here running on a surface of the substrate).

The invention is defined by the features of the independent claim(s). Preferred embodiments are defined in the dependent claims. Any reference numerals in the claims are intended to be non-limiting for their scope.

Some preferred embodiments have been shown in the foregoing, but it should be stressed that the invention is not limited to these, but may be embodied in other ways within the subject-matter defined in the following claims.

REFERENCES

[Bardal; 1994] Einar Bardal, 'Korrosjon og korrosjonsvern', Tapir Forlag, Trondheim, Norway, 2nd edition, 1994

U.S. Pat. No. 7,097,746 (ADVANCED BIONICS) Aug. 29, 2006

The invention claimed is:

1. A portable device comprising
a substrate,
a number of electronic components mounted on said substrate,
a battery comprising an anode and a cathode for energizing at least some of the electronic components, and
a pattern of electrical conductors connecting the electronic components and the battery,
wherein the portable device further comprises
a sacrificial anode implemented as an SMD-component adapted for being surface mounted on the substrate.

2. The portable device according to claim 1 wherein a distance between the sacrificial anode and the substrate—when the SMD-component comprising the sacrificial anode is initially mounted on the substrate—is adapted to soak up electrolytic solution via capillary effects.

3. The portable device according to claim 1 wherein the sacrificial anode is adapted for protecting an electric contact terminal connected to the battery.

4. The portable device according to claim 3 wherein the sacrificial anode is electrically connected to the anode or cathode of the battery.

5. The portable device according to claim 1 wherein the sacrificial anode comprises a metal that is less noble—with a view to the activity series—than the metal constituting the major part of the item to be protected against corrosion by the sacrificial anode.

6. The portable device according to claim 1 wherein the sacrificial anode comprises a metal plate of thickness less than 5 mm and an area less than 25 mm$^2$.

7. The portable device according to claim 1 wherein the portable device is a listening device.

8. The portable device according to claim 1 wherein the SMD-component comprising the sacrificial anode further comprises a reservoir for containing excess electrolytic solution.

9. The portable device according to claim 8 wherein at least a part of the sacrificial anode comprises a multitude of reservoirs.

10. The portable device according to claim 8 wherein at least a part of the sacrificial anode comprises an array of reservoirs.

11. The portable device according to claim 8 wherein the SMD-component comprising the sacrificial anode is adapted to allow air to escape from the reservoir in that the SMD-component comprises one or more openings.

12. The portable device according to claim 1 wherein the sacrificial anode is fully or partially formed as a web or mesh.

13. The portable device according to claim 1 wherein the sacrificial anode is mounted on the substrate.

14. A portable device comprising
a substrate,
a number of electronic components, and
a battery comprising an anode and a cathode for energizing at least some of the components,
wherein the portable device further comprises a sacrificial anode implemented as a component adapted for being surface mounted on the substrate,
wherein the sacrificial anode is fully or partially formed as a web or mesh.

15. The portable device according to claim 14 wherein the component comprising the sacrificial anode is an SMD component.

16. A method of protecting a portable device against corrosion, the method comprising:
providing a substrate;
mounting a number of electronic components on said substrate;
providing a battery comprising an anode and a cathode for energizing at least some of the electronic components;
providing a pattern of electrical conductors connecting the electronic components and the battery;
providing a sacrificial anode; and
providing that the sacrificial anode is formed as a surface mount device (SMD).

17. The method according to claim 16 comprising providing that the sacrificial anode comprises a metal that is less noble—with a view to the activity series—than the metal constituting the major part of the item to be protected against corrosion by the sacrificial anode; and electrically connecting the sacrificial anode to the item to be protected against corrosion.

18. The method according to claim 16 comprising providing that the sacrificial anode is mounted on the substrate.

19. The method according to claim 16 comprising electrically connecting the sacrificial anode to the anode of the battery.

20. The method according to claim 16 comprising providing that a distance between the sacrificial anode and the substrate—when the component is initially mounted on the substrate—is adapted to provide that electrolytic solution is soaked up via capillary effects.

21. The method according to claim 16 wherein the sacrificial anode is fully or partially formed as a web or mesh.

* * * * *